United States Patent
Dai et al.

(10) Patent No.: US 12,018,283 B2
(45) Date of Patent: Jun. 25, 2024

(54) METHOD FOR PRODUCING INSULIN-PRODUCING CELLS

(71) Applicants: KATAOKA CORPORATION, Kyoto (JP); Kyoto Prefectural Public University Corporation, Kyoto (JP)

(72) Inventors: Ping Dai, Kyoto (JP); Yukimasa Takeda, Kyoto (JP); Yoshinori Harada, Kyoto (JP); Junichi Matsumoto, Kyoto (JP); Ayumi Kusaka, Kyoto (JP)

(73) Assignees: KATAOKA CORPORATION, Kyoto (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 400 days.

(21) Appl. No.: 16/962,190

(22) PCT Filed: Jan. 24, 2019

(86) PCT No.: PCT/JP2019/002194
§ 371 (c)(1),
(2) Date: Jul. 14, 2020

(87) PCT Pub. No.: WO2019/151098
PCT Pub. Date: Aug. 8, 2019

(65) Prior Publication Data
US 2021/0062155 A1   Mar. 4, 2021

(30) Foreign Application Priority Data
Jan. 30, 2018 (JP) .................................. 2018-013303

(51) Int. Cl.
*C12N 5/071* (2010.01)
(52) U.S. Cl.
CPC ...... *C12N 5/0676* (2013.01); *C12N 2501/999* (2013.01); *C12N 2506/1307* (2013.01)
(58) Field of Classification Search
CPC ............ C12N 5/0676; C12N 2501/999; C12N 2506/1307; A61K 35/39; G01N 33/507; G01N 33/5073
See application file for complete search history.

(56) References Cited

U.S. PATENT DOCUMENTS

| | | | |
|---|---|---|---|
| 8,859,286 B2 * | 10/2014 | Agulnick | C12N 5/0678 435/377 |
| 9,371,516 B2 * | 6/2016 | Xu | A61K 9/1652 |
| 2015/0322406 A1 | 11/2015 | Behrens et al. | |
| 2016/0272944 A1 * | 9/2016 | Ding | A61K 35/39 |

FOREIGN PATENT DOCUMENTS

WO    WO-2017019702 A1 *   2/2017   ......... A01K 67/0271

OTHER PUBLICATIONS

Qin, H., Zhao, A., Fu, X., "Small molecules for reprogramming and transdifferentiation," Cell Mol Life Sci. 2017, 74(19): 3553-75, published Jul. 11, 2017 (Year: 2017).*
Kassem, D. H., et al., "Exendin-4 enhances the differentiation of Wharton's jelly mesenchymal stem cells into insulin-producing cells through activation of various β-cell markers," Stem Cell Research & Therapy 7: 108. doi: 10.1186/s13287-016-0374-4. Epub Aug. 11, 2016. (Year: 2016).*
Wang, X., et al., "Resveratrol Exerts Dosage-Dependent Effects on the Self-Renewal and Neural Differentiation of hUC-MSCs," Molecules and Cells 39(5):418-25. doi: 10.14348/molcells.2016.2345. Epub Apr. 25, 2016. (Year: 2016).*
Ebersolt, C., et al., "Inhibition of brain adenylate cyclase by A1 adenosine receptors: pharmacological characteristics and locations," Brain Research 267(1): 123-129. doi: 10.1016/0006-8993(83)91045-4. Published May 9, 1983 (Year: 1983).*
Lim, K. T., et al., "Small Molecules Facilitate Single Factor-Mediated Hepatic Reprogramming," Cell Reports 15(4):814-829. doi: 10.1016/j.celrep.2016.03.071. Epub Apr. 14, 2016. (Year: 2016).*
Selenica, M-L, et al., "Efficacy of small-molecule glycogen synthase kinase-3 inhibitors in the postnatal rat model of tau hyperphosphorylation," British Journal Pharmacology 152(6): 959-979. doi: 10.1038/sj.bjp.0707471. Epub Oct. 1, 2007. (Year: 2007).*
Yang, E., et al., "The Expression of DNMT1 in Pathologic Scar Fibroblasts and the Effect of 5-aza-2-Deoxycytidine on Cytokines of Pathologic Scar Fibroblasts," Wounds 26(5): 139-146. (Year: 2014).*
Portilho, N. A., et al., "The DNMT1 inhibitor GSK-3484862 mediates global demethylation in murine embryonic stem cells," Epigenetics Chromatin 14(1): 56. doi: 10.1186/s13072-021-00429-0. (Year: 2021).*
Shangtao Cao et al., "Chemical reprogramming of mouse embryonic and adult fibroblast into endoderm lineage," The Journal of Biological Chemistry, vol. 292, No. 46, 2017, 19122-19132, The American Society for Biochemistry and Molecular Biology, Inc.
Claudia Cavelti-Weder et al., "Direct Reprogramming for Pancreatic Beta-Cells Using Key Developmental Genes," Current Pathobiology Reports, vol. 3, No. 1, Mar. 1, 2015, pp. 57-65, doi: 10.1007/s40139-015-0068-0.

(Continued)

*Primary Examiner* — Tracy Vivlemore
*Assistant Examiner* — Eric J Rogers
(74) *Attorney, Agent, or Firm* — Morgan, Lewis & Bockius LLP

(57) ABSTRACT

The present invention chiefly aims to provide a process for directly inducing insulin-producing cells from somatic cells without performing artificial gene transfer. The present invention can include a process for producing an insulin-producing cell by inducing differentiation directly from a somatic cell, the process comprising a step of culturing the somatic cell in the presence of a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof. The insulin-producing cells obtained by the present invention are useful in regenerative medicine and the like.

13 Claims, 5 Drawing Sheets
(1 of 5 Drawing Sheet(s) Filed in Color)

(56) References Cited

OTHER PUBLICATIONS

Ping Dai et al., "Highly efficient direct conversion of human fibroblasts to neuronal cells by chemical compounds," Journal of Clinical Biochemistry and Nutrition, vol. 56, No. 3, May 2015, pp. 166-170.

Ke Li et al., "Small Molecules Facilitate the Reprogramming of Mouse Fibroblasts into Pancreatic Lineages," Cell Stem Cell, vol. 14, Feb. 6, 2014, pp. 228-236, Elsevier Inc.

Jun Xu et al., "Direct Lineage Reprogramming: Strategies, Mechanisms, and Applications," Cell Stem Cell, vol. 16, Feb. 5, 2015, pp. 119-134, Elsevier Inc.

Saiyong Zhu et al., "Human pancreatic beta-like cells converted from fibroblasts," Nature Communications, 7, Article No. 10080, 2016, pp. 1-13, doi: 10.1038/ncomms10080.

Begum Aydin et al., "Cell Reprogramming: The Many Roads to Success," Annual Review of Cell and Developmental Biology, vol. 35, pp. 433-452, 2019.

Yanbin Fu et al., "Direct reprogramming of mouse fibroblasts into cardiomyocytes with chemical cocktails," Cell Research, vol. 25, pp. 1013-1024, 2015.

Connor Lewis et al., "Direct Reprogramming Facilitated by Small Molecules," Journal of Stem Cell and Transplantation Biology, vol. 1, Issue 1, 270000103, 6 pages, 2015, Elyns Publishing Group, ISSN: 2469-5157.

Xiaojie Ma et al., "Chemical strategies for pancreatic β cell differentiation, reprogramming, and regeneration," Acta Biochimica et Biophysica Sinica, vol. 49, Issue 4, pp. 289-301, 2017, Oxford University Press.

Yukimasa Takeda et al., "Chemical compound-based direct reprogramming for future clinical applications," Bioscience Reports, vol. 38, BSR20171650, 2018, Portland Press.

Saiyong Zhu et al., "Human pancreatic beta-like cells converted from fibroblasts," Nature Communications, vol. 7, Article No. 10080, 13 pages, 2016.

The International Bureau of WIPO, "International Preliminary Report on Patentability," issued in International Application No. PCT/JP2019/002194, of which U.S. Appl. No. 16/962,190 is a U.S. national phase entry, with a dated Aug. 4, 2020, 12 pages (7 pages of English translation of International Preliminary Report on Patentability, and 5 pages of original International Preliminary Report on Patentability).

Ping Dai et al., "Direct Reprogramming by Small Molecules for Regenerative Medicine," Journal of Kyoto Prefectural University of Medicine, vol. 127, No. 1, 2018, pp. 1-12.

* cited by examiner

[Figure 1]

[Figure 3]
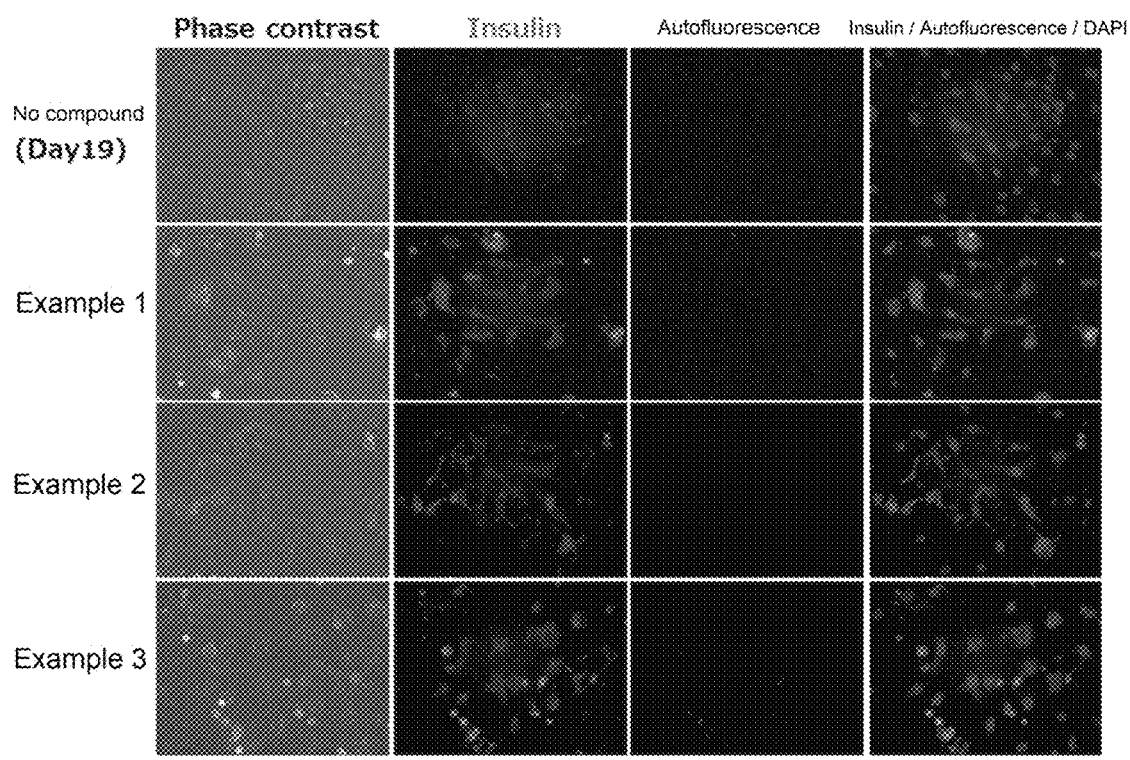

[Figure 4]
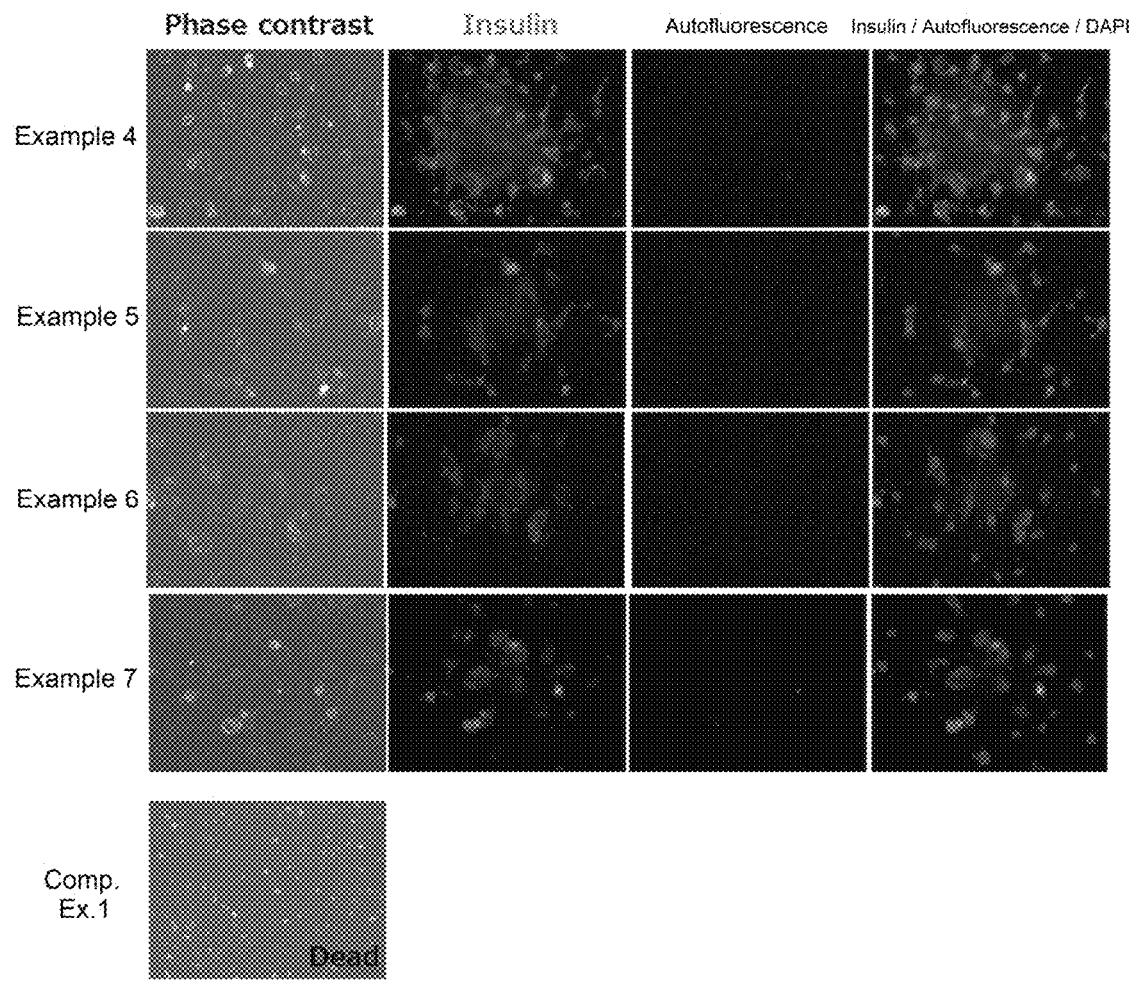
[Figure 5]
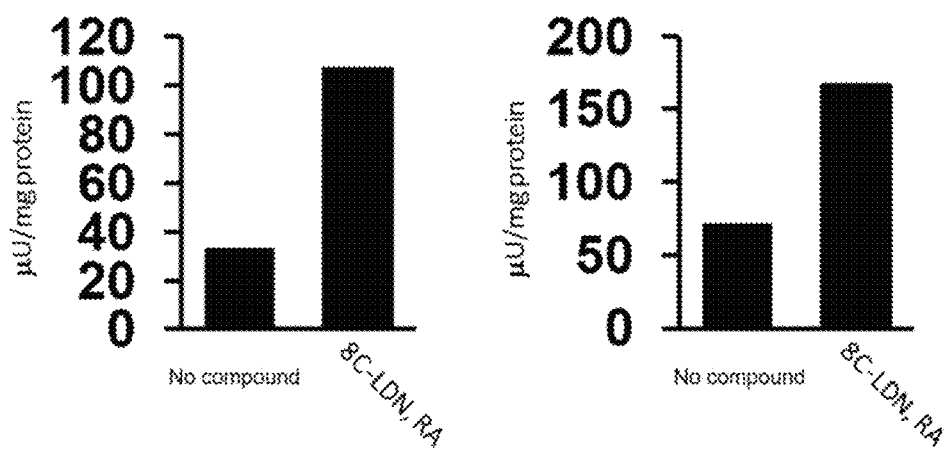

[Figure 6]
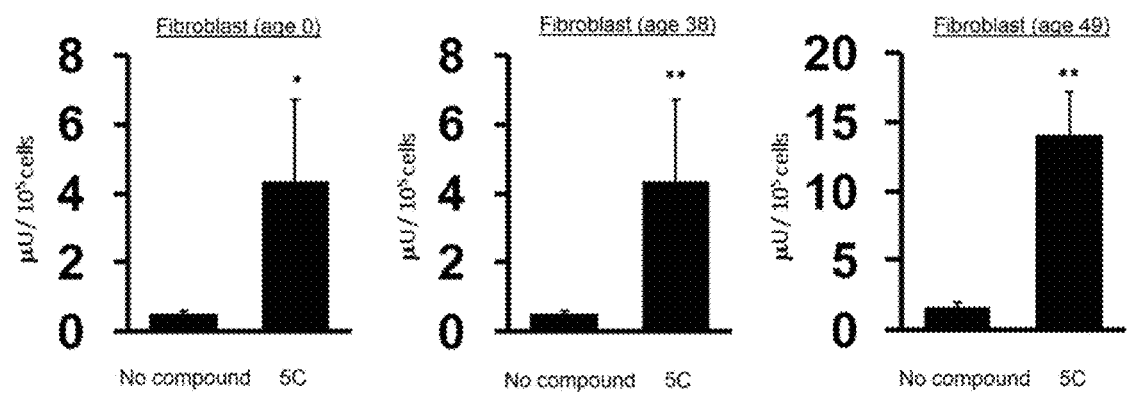

METHOD FOR PRODUCING INSULIN-PRODUCING CELLS

CROSS-REFERENCE TO RELATED APPLICATIONS

This application claims priority from Japanese Application No. 2018-13303, filed Jan. 30, 2018, the disclosure of which is incorporated herein in its entirety.

TECHNICAL FIELD

The present invention belongs to the field of regenerative medicine or direct reprogramming from somatic cells. The present invention relates in the field to a process for direct production of insulin producing cells from somatic cells with a low molecular weight compound, and to low molecular weight compound inducible insulin producing cells (ci-IPCs: chemical compound-induced Insulin-producing cells) produced by such a process. The present invention further relates to the insulin producing cells and compositions that can be used for processes of producing the insulin producing cells.

BACKGROUND OF THE INVENTION

Recent developments in cell-related research, particularly in pluripotent cells, have made it possible to obtain therapeutic cells in the quality and quantity available for transplantation into an individual. For several diseases, attempts have been initiated to transplant cells that are effective for treatment into patients.

The cells of the mesenchymal system form various organs of the living body such as muscle, bone, cartilage, bone marrow, fat and connective tissue, and are promising as materials of regenerative medicine. Mesenchymal stem cells (MSCs) are undifferentiated cells present in tissues such as bone marrow, adipose tissue, blood, placentas and umbilical cord. Because of their ability to differentiate into cells belonging to the mesenchymal system, mesenchymal stem cells have attracted attention as a starting material in the production of these cells. Regenerative medicine using mesenchymal stem cells themselves for reconstruction of bone, cartilage, myocardium, etc. is also being investigated.

Meanwhile, methods have also been reported to convert somatic cells such as fibroblasts directly into other cells. For example, it is known to obtain a neural cell by cultivating the fibroblast with a chemical substance (Non-Patent Document 1).

For insulin-secreting pancreatic β-cells, in addition to differentiation induction from iPS cells or ES cells to human pancreatic β-cells, it has been reported that pancreatic β-cells were induced directly from endodermal cells like pancreatic α-cells, pancreatic acinar cells, pancreatic ductal gland cells, small intestinal crypt cells, hepatocytes, and cholangiocytes by using Pdx1, Ngn3, and MafA, which are pancreatic β-cell-specific transcription factors (Non-Patent Document 2). In addition, direct induction from murine fetal fibroblasts (MEFs) and human dermal fibroblasts to pancreatic β cells using Yamanaka-4 factors has been reported (Non-Patent Documents 3 and 4). Furthermore, it has been reported that endoderm progenitor cells were produced from murine fetal fibroblasts (MEFs) by low molecular weight compounds and differentiated from the cells into pancreatic endocrine cells (Non-Patent Document 5).

PRIOR ART

Non-Patent Document

Non-Patent Document 1: Journal of Clinical Biochemistry and Nutrition, 2015, Vol. 56, No. 3, pp. 166-170
Non-Patent Document 2: Current Pathobiology Reports, 2016, Vol. 3, pp. 57-65
Non-Patent Document 3: Cell Stem Cell, 2014, 14, pp. 228-236
Non-Patent Document 4: Nature Communications, 2016, Vol. 7, p. 10080
Non-Patent Document 5: Journal of Biological Chemistry, 2017, 292, pp. 19122-19132

SUMMARY OF THE INVENTION

Problem to be Solved by the Present Invention

As in the method described in Non-Patent Document 1, a method of directly converting a somatic cell into a desired cell without gene transfer may be an effective option as a means of obtaining a therapeutic cell. Pancreatic β cells have also been reported to be converted directly from somatic cells, as described above, but these inventions induce them by introducing specific genes into endoderm line cells that are developmentally close.

It is a main object of the present invention to provide a process for directly inducing insulin-producing cells from somatic cells by a combination of small molecule compounds without performing artificial gene transfer, that is, a new process capable of directly producing insulin-producing cells from somatic cells by a composition of certain small molecule compounds.

Means for Solving the Problems

As a result of intensive investigation, the present inventors have found that somatic cells can be directly converted into insulin-producing cells by culturing the somatic cells in the presence of a certain small molecule inhibitor or the like, and thus the present invention has been completed.

The present invention can include the following, for example.

[1] A process for producing an insulin-producing cell by inducing differentiation directly from a somatic cell, the process comprising a step of culturing the somatic cell in the presence of a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof.

[2] The process producing an insulin-producing cell according to the above [1], wherein the said step is a step of cultivating a somatic cell in the presence of a PI3K inhibitor and a cAMP inducer, and five members selected from the group consisting of a GSK3 inhibitor, a TGF-β inhibitor, a BMP inhibitor, a p53 inhibitor, a Notch inhibitor and a RAR agonist, or all members thereof.

[3] The process for producing an insulin-producing cell according to the above [1], wherein the said step is a step of culturing a somatic cell in the presence of a GSK3 inhibitor, a TGF-β inhibitor, a p53 inhibitor, a Notch inhibitor, a RAR agonist, a PI3K inhibitor, and a cAMP inducer.

[4] The process for producing an insulin-producing cell according to the above [1] or [2], wherein the BMP inhibitor is LDN193189.

[5] The process for producing an insulin-producing cell according to any one of the above [1] to [3], wherein the GSK3 inhibitor is CHIR99021, the TGF-β inhibitor is SB431542, the p53 inhibitor is pifithrin, the PI3K inhibitor is LY294002, the Notch inhibitor is DAPT, the RAR agonist is retinoic acid, or the cAMP inducer is forskolin.

[6] A process for producing an insulin-producing cell by inducing differentiation directly from a somatic cell, the process comprising a step of culturing the somatic cell in the presence of a GSK3 inhibitor, a TGF-β inhibitor, a PI3K inhibitor, a Notch inhibitor, and a cAMP inducer.

[7] The process for producing an insulin-producing cell according to the above [6], wherein the GSK3 inhibitor is CHIR99021, the TGF-β inhibitor is SB431542, the PI3K inhibitor is LY294002, the Notch inhibitor is DAPT, or the cAMP inducer is forskolin.

[8] The process for producing an insulin-producing cell according to any one of the above [1] to [7], wherein the somatic cell is a fibroblast.

[9] An insulin-producing cell produced from the process for producing an insulin-producing cell according to any one of the above [1] to [8].

[10] A composition for producing an insulin-producing cell by inducing differentiation directly from a somatic cell, the composition comprising a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof.

[11] The composition according to the above [10], comprising a PI3K inhibitor and cAMP inducer, and five members selected from the group consisting of a GSK3 inhibitor, a TGF-β inhibitor, a BMP inhibitor, a p53 inhibitor, a Notch inhibitor and a RAR agonist, or all members thereof.

[12] The composition according to the above [10], comprising a GSK3 inhibitor, a TGF-β inhibitor, a p53 inhibitor, a Notch inhibitor, a RAR agonist, a PI3K inhibitor, and a cAMP inducer.

[13] The composition according to the above [10] or [11], wherein the BMP inhibitor is LDN193189.

[14] The composition according to any one of the above [10] to [12], wherein the GSK3 inhibitor is CHIR99021, the TGF-β inhibitor is SB431542, the p53 inhibitor is pifithrin, the PI3K inhibitor is LY294002, the Notch inhibitor is DAPT, the RAR agonist is retinoic acid, or the cAMP inducer is forskolin.

[15] A composition for producing an insulin-producing cell by inducing differentiation directly from a somatic cell, comprising a GSK3 inhibitor, a TGF-β inhibitor, a PI3K inhibitor, a Notch inhibitor, and a cAMP inducer.

[16] The composition according to the above [15], wherein the GSK3 inhibitor is CHIR99021, the TGF-β inhibitor is SB431542, the PI3K inhibitor is LY294002, the Notch inhibitor is DAPT, or the cAMP inducer is forskolin.

[17] The composition according to any one of the above [10] to [16], wherein the somatic cell is a fibroblast.

Effect of the Invention

According to the present invention, insulin-producing cells can be produced from somatic cells without gene transfer. The insulin-producing cells obtained by the present invention are useful in regenerative medicine and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 is culture photographs (Phase contrast) of cells on the $19^{th}$ day after culturing by adding the compound, and the immune staining photographs.

FIG. 4 is culture photographs (Phase contrast) of cells on the $19^{th}$ day after culturing by adding the compound and the immune staining photographs.

FIG. 5 represents the amount of insulin secreted into the supernatant in the left side figure, and the amount of insulin secreted remaining in cells in the right figure. In each figure, the vertical axis shows the amount of secretion (μU/mg) per mg of total protein. In each figure, the results of the case where the low molecular weight compound is added are shown in the right column and the results of the case where the low molecular weight compound is not added are shown in the left column.

Figure 1:
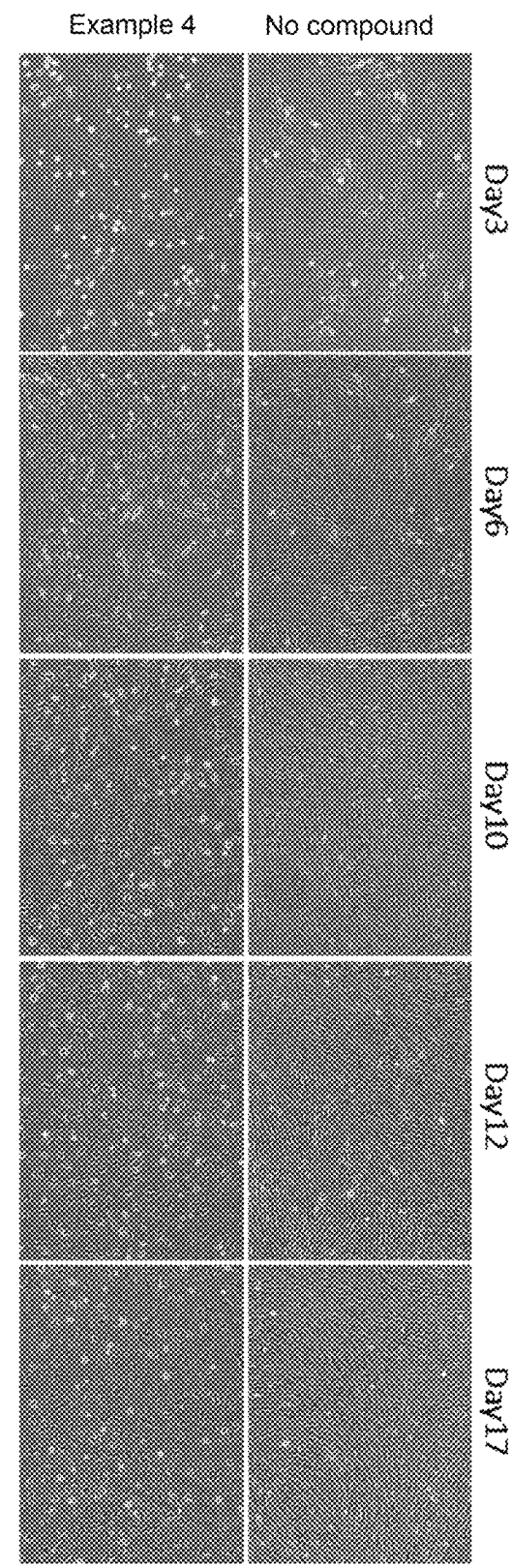
FIG. 1 is culture photographs of cells. The five photographs on the left represent the results when the combination compound of Example 4 was added, and the five photographs on the right represent the results when the compound was not added. Day 3, 6, 10, 12, and 17 represent the $3^{rd}$ day, the $6^{th}$ day, the $10^{th}$ day, the $12^{th}$ day, and the $17^{th}$ day, respectively, after culturing with the compound.

The vertical axis in each figure of FIG. 6 shows the amount of secretion ($\mu U/10^5$ of cells) per $10^5$ of cells. In each figure, the results of the case where the low molecular weight compound is added are shown in the right column and the results of the case where the low molecular weight compound is not added are shown in the left column.

EMBODIMENT FOR CARRYING OUT THE PRESENT INVENTION

Hereinafter is described about the present invention in detail.

1 Process for Producing Insulin-Producing Cells

The process for producing insulin-producing cells, according to the present invention (hereinafter referred to as the "present invention process"), is a process for producing an insulin-producing cell by inducing differentiation directly from a somatic cell, characterized by comprising a step of culturing the somatic cell in the presence of a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof.

In the present invention, it is preferred that the above step is a step of culturing a somatic cell in the presence of a PI3K inhibitor and a cAMP inducer, and five members selected from the group consisting of a GSK3 inhibitor, a TGF-β inhibitor, a BMP inhibitor, a p53 inhibitor, a Notch inhibitor and a RAR agonist, or all members thereof. It is more preferred that the above step is a step of culturing a somatic cell in the presence of a GSK3 inhibitor, a TGF-β inhibitor, a p53 inhibitor, a Notch inhibitor, a RAR agonist, a PI3K inhibitor, and a cAMP inducer. In the present invention process, it is particularly preferable to culture a somatic cell in the presence of a cAMP inducer or the inducer and a PI3K inhibitor.

Further, the present invention can also include a process for producing an insulin-producing cell by inducing differentiation directly from a somatic cell, characterized by comprising a step of culturing the somatic cell in the presence of a GSK3 inhibitor, a TGF-β inhibitor, a PI3K inhibitor, a Notch inhibitor, and a cAMP inducer. Hereinafter, such a process is also referred to as the present invention process.

In the present invention process, the somatic cell may be cultured in the presence of at least any combination of the above, and the somatic cell may optionally be cultured in the presence of other inhibitors, inducers, or the like to produce an insulin-producing cell, if necessary.

Each of the above inhibitors, inducers, and the like may be alone or a combination of two or more kinds.

Specific inhibitors and the like may have two or more kinds of inhibitory effects, and in this case, one inhibitor and the like may be considered to include a plurality of inhibitors and the like.

1.1 Somatic Cells

Cells of an organism can be classified into somatic and germ cells. Any somatic cell can be used as a starting material in the process of the present invention. The somatic cell is not particularly limited, and may be either a primary cell taken from a living body or a cell that has been strained. Somatic cells at various stages of differentiation, e.g., terminally differentiated somatic cells (e.g., fibroblasts, umbilical vein endothelial cells (HUVEC), hepatocellulars (Hepatocytes), bile duct cells (Biliary cells), pancreatic alpha cells (Pancreatic α cells), pancreatic acinar cells (Acinar cells), pancreatic ductal gland cells (Ductal cells), small intestinal crypt cells (Intestinal crypt cells), etc.), somatic cells on the way to terminal differentiation (e.g., mesenchymal stem cells, neural stem cells, endodermal progenitor cells, etc.), or initialized and pluripotent somatic cells can be used. The somatic cells that can be used in the method of the present invention include any somatic cells, for example, cells of the hematopoietic system (various lymphocytes, macrophages, dendritic cells, bone marrow cells, etc.), cells derived from organs (hepatocellulars, splenocytes, pancreatic cells, kidney cells, lung cells, etc.), cells of the muscle tissue system (skeletal muscle cells, smooth muscle cells, myoblasts, cardiomyocytes, etc.), fibroblasts, nerve cells, osteoblasts, chondrocytes, endothelial cells, interstitial cells, adipocytes (brown adipocytes, white adipocytes, etc.), and the like. The method of the present invention can also be applied to precursor cells and cancer cells of these cells. Preferably, fibroblasts or mesenchymal stem cells can be used.

Examples of the source of the above-mentioned somatic cells include, but are not limited to, humans, non-human mammals, and non-mammals (birds, reptiles, amphibians, fish, etc.). As the source of the somatic cells, humans and non-human mammals are preferable, and humans are particularly preferable. When insulin-producing cells are produced by the present invention process for administration to humans, preferably somatic cells harvested from a donor that matches or is similar to the type of histocompatibility antigen with the recipient can be used. Somatic cells harvested from the recipient itself may be used for the production of insulin-producing cells.

1.2 Inhibitors, Etc. According to the Present Invention
1.2.1 GSK3 Inhibitors GSK3 (Glycogen Synthase Kinase-3) was found as a protein kinase that phosphorylates and inactivates glycogen synthase. In mammals, GSK3 is classified into two isoforms: α of 51 kDa (GSK3α) and β of 47 kDa (GSK3β). GSK3 has the activity of phosphorylating various proteins and is involved not only in glycogen metabolism but also in physiological phenomena such as cell division and cell growth.

The term "in the presence of a GSK3 inhibitor" means under a culture condition capable of inhibiting GSK3, and the means thereof is not particularly limited, and substances that inhibit the activity of GSK3, for example, a GSK3 signal inhibiting means such as anti GSK3 antibodies or GSK3 inhibitors can be used. Since GSK3 loses its activity when phosphorylated at certain sites, the phosphorylation-promoting means as mentioned above can also be used to inhibit GSK3 signaling.

Although not particularly limited in the present invention, as the GSK3 inhibitor, for example, the following compounds can be used. Preferably, CHIR99021 can be used.
CHIR99021 (CAS No.: 252917-06-9)

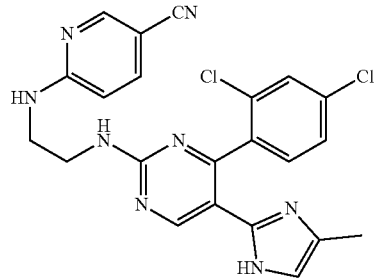

[Chemical 1]

BIO((2'Z,3'E)-6-Bromoindirubin-3'-oxime) (CAS No.: 667463-62-9)
Kenpaullone (CAS No.: 142273-20-9)
A1070722 (CAS No.: 1384424-80-9)
SB216763 (CAS No.: 280744-09-4)
CHIR98014 (CAS No.: 556813-39-9)
TWS119 (CAS No.: 601514-19-6)
Tideglusib (CAS No.: 865854-05-3)
SB415286 (CAS No.: 264218-23-7)
Bikinin (CAS No.: 188011-69-0)
IM-12 (CAS No.: 1129669-05-1)
1-Azakenpaullone (CAS No.: 676596-65-9)
LY2090314 (CAS No.: 603288-22-8)
AZD1080 (CAS No.: 612487-72-6)
AZD2858 (CAS No.: 486424-20-8)
AR-A014418 (CAS No.: 487021-52-3)
TDZD-8 (CAS No.: 327036-89-5)
Indirubin (CAS No.: 479-41-4)

The concentration of the GSK3 inhibitor may be appropriately determined, and is not particularly limited, and may be used, for example, in the range of 0.1 μmol/L to 20 μmol/L, preferably in the range of 0.5 μmol/L to 10 μmol/L.

1.2.2 TGF-β Inhibitors

There are three types of TGF-β (transforming growth factor-β), TGF-β1, TGF-β2, and TGF-β3, which are produced from almost all cells. TGF-β is involved in a wide variety of cellular functions, including cell growth, transformation, differentiation, development, and control of apoptosis, such as suppressing the growth of epithelial cells and many other cells.

The term "in the presence of a TGF-β inhibitor" means under a culture condition capable of inhibiting TGF-β, and the means thereof is not particularly limited, and any means capable of inhibiting TGF-β can be used. Substances that act directly on TGF-β to inhibit its function (e.g., anti TGF-β antibodies and other drugs), agents that inhibit the production of TGF-β themselves, or the like can be used in the present invention. TGF-β can also be inhibited by inhibiting signaling that involves TGF-β upstream.

Although not particularly limited in the present invention, as the TGF-β inhibitor, for example, the following compounds can be used. Preferably, SB431542 or RepSox can be used.

SB431542 (CAS No.: 301836-41-9)

[Chemical 2]

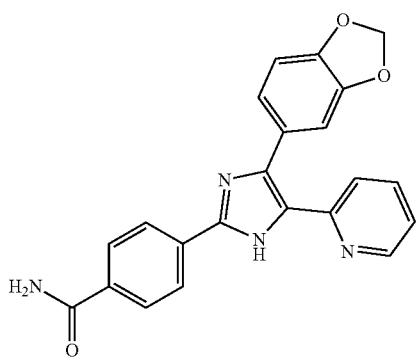

A83-01 (CAS No.: 909910-43-6)

[Chemical 3]

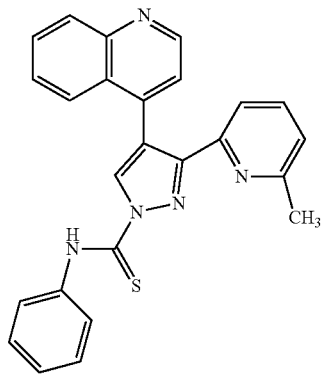

RepSox (CAS No.: 446859-33-2)

[Chemical 4]

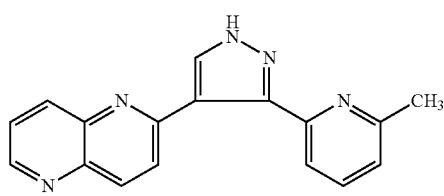

LY364947 (CAS No.: 396129-53-6)
SB525334 (CAS No.: 356559-20-1)
SD208 (CAS No.: 627536-09-8)
Galunisertib (LY2157299) (CAS No.: 700874-72-2)
LY2109761 (CAS No.: 700874-71-1)
SB505124 (CAS No.: 694433-59-5)
GW788388 (CAS No.: 452342-67-5)
EW-7197 (CAS No.: 1352608-82-2)

The concentration of the TGF-β inhibitor may be appropriately determined, and is not particularly limited, and may be used, for example, in the range of 0.1 μmol/L to 30 μmol/L, preferably in the range of 0.5 μmol/L to 10 μmol/L.

1.2.3 BMP Inhibitors

BMPs (Bone Morphogenetic Proteins) are growth factors belonging to TGF-β superfamily that control embryonic and tissue development, cell differentiation, cell death, and so on. BMPs bind to type I and type II receptors on the plasma membrane to form heterotetramers, which transduce BMP signals into the nucleus via phosphorylation of the transcription factor SMAD. A lot of BMP inhibitors inhibit the phosphorylation of SMAD by ALK (Activin receptor-like kinase)-2,3,6, a type I receptor activated by BMP binding.

The term "in the presence of a BMP inhibitor" means under a culture condition capable of inhibiting the BMP signaling pathway, and the means thereof is not particularly limited, and any means capable of inhibiting the BMP signaling pathway can be used. Substances that directly act on BMPs and BMP receptors to inhibit their function (e.g., anti-BMP antibodies, other drugs), or agents that suppress their expression, or the like can be used in the present invention. The BMP signaling pathway can be also inhibited by inhibiting the expression of SMAD transcription factors and their post-translational modifications downstream of signaling in which BMPs are involved.

Although not particularly limited in the present invention, as the BMP inhibitor, for example, the following compounds can be used. Preferably, LDN193189 can be used.

LDN193189 (CAS No.: 1062368-24-4)

[Chemical 5]

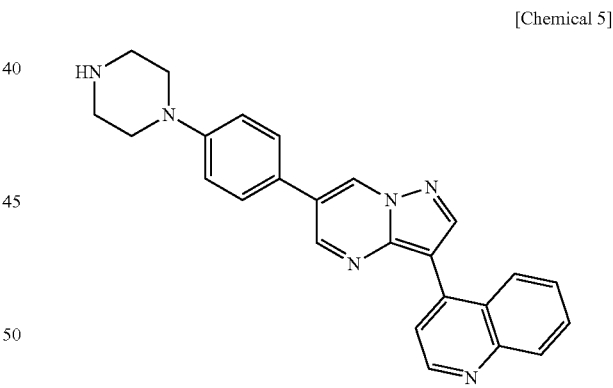

DMH1 (CAS No.: 1206711-16-1)
K02288 (CAS No.: 1431985-92-0)
LDN212854 (CAS No.: 1432597-26-6)
LDN193189 HCl (CAS No.: 1062368-62-0)
ML347 (CAS No.: 1062368-49-3)
LDN214117 (CAS No.: 1627503-67-6)

The concentration of the BMP inhibitor may be appropriately determined, and is not particularly limited, and may be used, for example, in the range of 0.1 μmol/L to 10 μmol/L, preferably 0.5 μmol/L to 5 μmol/L.

1.2.4 p53 Inhibitors p53 is one of the most important tumor suppressor genes, which suppresses cell proliferation and plays an important role in tumor suppression. Also, it responds to various stresses to activate the target gene, and it is a starting point for cell cycle arrest, apoptosis, DNA repair, cell senescence, etc.

The term "in the presence of a p53 inhibitor" means under a culture condition capable of inhibiting p53, and the means thereof is not particularly limited, and any means capable of inhibiting p53 can be used. Substances that directly act on p53 to inhibit its function (for example, an anti-p53 antibody or other drug), agents that suppress the production of p53 itself, or the like can be used in the present invention. p53 can also be inhibited by inhibiting at upstream thereof signaling in which p53 is involved.

Although not particularly limited in the present invention, as the p53 inhibitor, for example, the following compounds can be used. Preferably, pifithrin or pifithrin-α can be used.

Pifithrin-α (CAS No.: 63208-82-2)

[Chemical 6]

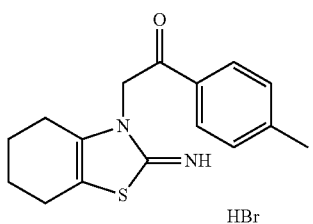

Pifithrin-β (CAS No.: 511296-88-1)
Pifithrin-μ (CAS No.: 64984-31-2)
NSC66811 (CAS No.: 6964-62-1)
Nultin-3 (CAS No.: 548472-68-0)

The concentration of the p53 inhibitor may be appropriately determined, and is not particularly limited, and may be used, for example, in the range of 0.5 μmol/L to 30 μmol/L, preferably 1 μmol/L to 10 μmol/L.

1.2.5 cAMP Induction Agent cAMP (cyclic Adenosine Monophosphate) is a second messenger that is involved in a variety of intracellular signaling events. cAMP is produced intracellularly by cyclization of adenosine triphosphate (ATP) by adenylyl cyclase (adenylate cyclase).

The term "in the presence of a cAMP inducer" means under a culture condition capable of inducing cAMP, and the means thereof is not particularly limited, and any means capable of increasing intracellular cAMP concentrations, for example, can be used. Substances that can induce it by direct action on adenylate cyclase, which is an enzyme involved in the production of cAMP, substances that can promote the expression of adenylate cyclase, and substances that inhibit phosphodiesterase, which is an enzyme that degrades cAMP, can be used as means for increasing intracellular cAMP concentrations. Membrane permeable cAMP analogues such as dibutyryl cAMP or 8-bromo-cAMP, which are structural analogues of cAMP that have the same effect as cAMP in cells, can also be used.

Although not particularly limited in the present invention, the cAMP inducer (adenylate cyclase activating agents) can include forskolin (CAS No.: 66575-29-9), forskolin derivatives (for example, Japanese Patent Laid-Open No. 2002-348243), the following compounds, and the like. Preferably, forskolin can be used.

Forskolin (CAS No.: 66428-89-5)

[Chemical 7]

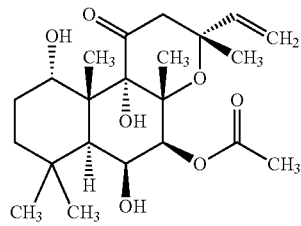

Isoproterenol (CAS No.: 7683-59-2)
NKH477 (CAS No.: 138605-00-2)
PACAP1-27 (CAS No.: 127317-03-7)
PACAP1-38 (CAS No.: 137061-48-4)

The concentration of the cAMP inducer may be appropriately determined, and is not particularly limited, and may be, for example, in the range of 0.2 μmol/L to 50 μmol/L, preferably 1 μmol/L to 30 μmol/L.

1.2.6 PI3K Inhibitors

PI3K (Phosphoinositide 3-kinase) is an enzyme that phosphorylates inositol phospholipids, and the phosphoinositides produced activate PDK1. PDK1 further phosphorylates AKTs and PDK1/AKT signaling pathway is activated. LY294002 is a PI3K selective inhibitor and inhibits activation of PDK1/AKT signaling pathway by suppressing the production of phosphoinositides.

The term "in the presence of a PI3K inhibitor" means under a culture condition capable of inhibiting PI3K, and the means thereof is not particularly limited, and any means capable of inhibiting PI3K can be used. Substances that act directly on PI3K to inhibit its function (e.g., anti PI3K antibodies, other drugs), agents that inhibit the production of PI3K themselves, or the like can be used in the present invention. PI3K can also be inhibited by inhibiting at upstream thereof signaling in which PI3K is involved.

Although not particularly limited in the present invention, as the PI3K inhibitor, for example, the following compounds can be used. Preferably, LY294002 can be used.

LY294002 (CAS No.: 154447-36-6)

[Chemical 8]

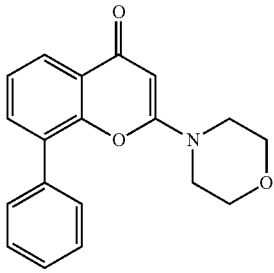

Buparlisib (CAS No.: 944396-07-0)
TGR-1202 (CAS No.: 1532533-67-7)
PI-103 (CAS No.: 371935-74-9)
IC-87114 (CAS No.: 371242-69-2)
Wortmannin (CAS No.: 19545-26-7)
ZSTK474 (CAS No.: 475110-96-4)
AS-605240 (CAS No.: 648450-29-7)
PIK-90 (CAS No.: 677338-12-4)
AZD6482 (CAS No.: 1173900-33-8)
Duvelisib (CAS No.: 1201438-56-3)

TG100-115 (CAS No.: 677297-51-7)
CH5132799 (CAS No.: 1007207-67-1)
CAY10505 (CAS No.: 1218777-13-9)
PIK-293 (CAS No.: 900185-01-5)
CZC24832 (CAS No.: 1159824-67-5)
Pilaralisib (CAS No.: 934526-89-3)
AZD8835 (CAS No.: 1620576-64-8)

The concentration of the PI3K inhibitor may be appropriately determined, and is not particularly limited, and may be used, for example, in the range of 0.1 μmol/L to 20 μmol/L, preferably in the range of 0.5 μmol/L to 10 μmol/L.

1.2.7 Notch Inhibitors

Notch is a single-pass transmembrane receptor, and is cleaved by γ-secretase and intracellular regions translocate to the nucleus to function as a transcription factor. DAPT is an inhibitor of γ-secretase and functions as an inhibitor of Notch signals by inhibiting Notch cleavage.

The term "in the presence of a Notch inhibitor" means under a culture condition capable of inhibiting Notch, and the means thereof is not particularly limited, and any means capable of inhibiting Notch can be used. Substances that act directly on Notch to inhibit its function (e.g., anti Notch antibodies, other drugs), agents that suppress the expression of Notch themselves, or the like can be used in the present invention. Notch can also be inhibited by inhibiting signaling in which Notch is involved.

Although not particularly limited in the present invention, as the Notch inhibitor, for example, the following compounds can be used. Preferably, DAPT can be used.
DAPT (CAS No.: 208255-80-5)

[Chemical 9]

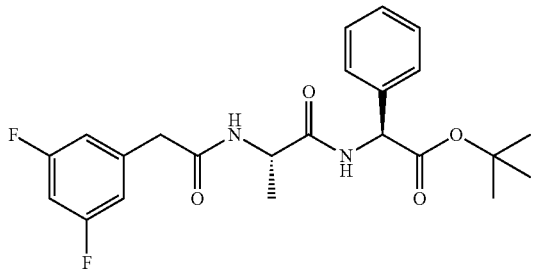

R04929097 (CAS No.: 847925-91-1)
FLI-06 (CAS No.: 313967-18-9)
Semagacestat (CAS No.: 425386-60-3)
Dibenzazepine (CAS No.: 209984-56-5)
PF-03084014 (CAS No.: 1290543-63-3)
IMR-1 (CAS No.: 310456-65-6)

The concentration of the Notch inhibitor may be appropriately determined, and is not particularly limited, and may be used, for example, in the range of 0.2 μmol/L to 30 μmol/L, preferably in the range of 1 μmol/L to 10 μmol/L.

1.2.8 RAR Agonists

RAR (Retinoic acid receptor, retinoic acid receptor) belongs to the nuclear receptor superfamily and is liganded by retinoic acid, and its transcriptional activity is activated. Since RAR has various functions in vivo and is closely related to cell differentiation in particular, a number of artificial synthetic agonists have been developed.

The term "in the presence of" a RAR agonise means under a culture condition capable of activating RAR, and the means thereof is not particularly limited, and any means capable of activating RAR can be used. Substances that act directly on RAR to operate its function, agents that promote expression of RAR itself, or the like can be used in the present invention. The functions of RAR can also be controlled by regulating transcription factors or transcription coupling factors that interact with RAR, or their expression and post-translational modifications, etc.

Although not particularly limited in the present invention, as the RAR agonist, for example, the following compounds can be used. Preferably, retinoic acid or CH55, AM580 can be used.
Retinoic acid (CAS No.: 302-79-4)
CH55 (CAS No.: 110368-33-7)
AM580 (CAS No.: 102121-60-8)
Tretinoin (CAS No.: 302-79-4)
Adapalene (CAS No.: 106685-40-9)
Bexarotene (CAS No.: 153559-49-0)
Tazarotene (CAS No.: 118292-40-3)
Tamibarotene (CAS No.: 94497-51-5)
[0077]

The concentration of the RAR agonist may be appropriately determined, and is not particularly limited, and may be used, for example, in the range of 0.05 μmol/L to 10 μmol/L, preferably 0.5 μmol/L to 5 μmol/L.

1.3 Somatic Cell Culture

The cultivation of the somatic cells in the present invention process may be carried out in the presence of various inhibitors (and, optionally, inducers or activating agents) described above by selecting the culture medium, temperature, and other conditions according to the type of somatic cells used. The medium can be selected from known media or commercially available media. For example, MEM (Minimum Essential Medium), DMEM (Dulbecco's Modified Eagle Medium), DMEM/F12, or a medium obtained by modifying MEM (Minimum Essential Medium), DMEM (Dulbecco's Modified Eagle Medium), which is a common medium, can be used by adding appropriate components (sera, proteins, amino acids, sugars, vitamins, fatty acids, antibiotics, and the like).

As the culture conditions, general cell culture conditions may be selected. Conditions such as 37° C. and 5% $CO_2$ are illustrated. It is preferred to change the medium at appropriate intervals during culture, preferably once every 1 to 7 days, more preferably once every 3 to 4 days. When the present invention process is carried out using fibroblasts as materials, insulin-producing cells appear in 8 to 10 days to 3 weeks at 37° C. and 5% $CO_2$. It is also possible to convert somatic cells, the number of which has been increased in advance, into insulin-producing cells by selecting somatic cells which can be easily cultured as the somatic cells to be used. Thus, the scaled-up production of insulin-producing cells is also easy.

Cell culture vessels such as plates, dishes, cell culture flasks, cell culture bags, and the like can be used for culturing somatic cells. As the cell culture bag, a bag having gas permeability is suitable. If large quantities of cells are required, a large culture vessel may be used. Culturing can be carried out either in an open system or in a closed system, but when administration of the obtained insulin-producing cell to a human or the like is intended, it is preferable to carry out culturing in a closed system.

In the present invention process, by culturing somatic cells in a medium containing various inhibitors and the like described above, it is possible to produce insulin-producing cells from somatic cells by one step of culturing.

1.4 Insulin-Producing Cells

The cell population containing insulin-producing cells can be obtained by the above-described present invention process. The insulin-producing cells produced by the present invention process are also within the scope of the present invention.

The insulin-producing cells produced by the present invention process are so-called low molecular weight chemical compound-induced insulin-producing cells (ciIPCs), which are derived directly from somatic cells by small molecule compounds, and are distinguished from insulin-producing cells derived from ES cells and iPS cells.

The insulin-producing cells produced by the present invention process can be detected, confirmed, and separated using, for example, morphological changes of the cells, characteristic properties of the insulin-producing cells, and specific markers (e.g., anti-insulin antibodies).

Quarantine methods (detection by antibodies) can be used for detection of specific markers, but detection of protein molecules may be carried out by quantitation of mRNA amount of protein molecules. Antibodies that recognize specific markers of insulin-producing cells are also useful for isolating and purifying insulin-producing cells obtained by the present invention process.

The insulin-producing cells produced by the present invention process can be used, for example, for tissue repair, improvement of blood insulin concentration, and the like. The insulin-producing cells produced by the present invention process can be used to produce pharmaceutical compositions for tissue repair and the like. Pancreas transplantation or islet transplantation has become a radical treatment for patients with type 1 diabetes, in whom insulin is poorly secretable, to relieve and cure their symptoms. In addition, the number of patients with type 2 diabetes mellitus is expected to increase further in Japan and overseas and cause medical costs to rise. Thus, transplantation of pancreatic β cells secreting insulin may be an effective therapy. As a means for treating pancreatic diseases such as diabetes mellitus, a process for producing insulin-producing cells and a process for transplanting insulin-producing cells have been developed. For example, transplantation of insulin-producing cells under the kidney capsule or transplantation into the liver via the portal vein is expected to be used for the treatment of severe pancreatic diseases such as diabetes mellitus.

When the insulin-producing cells produced by the present invention process are used as a pharmaceutical composition, the insulin-producing cells may be mixed with a pharmaceutically acceptable carrier by a conventional method to prepare a formulation in a form suitable for administration to an individual. Carriers include, for example, saline, distilled water for injection made isotonic with glucose and other adjuvants (e.g., D-sorbitol, D-mannitol, sodium chloride, etc.). In addition, buffers (e.g., phosphate buffer, sodium acetate buffer), analgesics (e.g., benzalkonium chloride, procaine hydrochloride, etc.), stabilizers (e.g., human serum albumin, polyethylene glycol, etc.), preservatives, antioxidants, and the like may be included.

The insulin-producing cells produced by the present invention process may further be a composition in combination with other cells or components effective for the functional exertion or the improvement of the engraftment of the insulin-producing cells.

Furthermore, the insulin-producing cells produced by the present invention process can be used for screening a drug candidate compound acting on the insulin-producing cells or for safety evaluation of the drug candidate compound. The insulin-producing cells are an important tool for assessing the toxicity of drug candidates. According to the present invention process, since a large number of insulin-producing cells can be obtained by one operation, it is possible to obtain a reproducible research result without being affected by a lot difference of cells.

2 Composition

A composition according to the present invention (hereinafter referred to as the "composition of the present invention") is a composition for producing an insulin-producing cell by inducing differentiation directly from a somatic cell, and is characterized by comprising a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof.

Preferably, the composition of the present invention comprises a PI3K inhibitor and cAMP inducer, and five members selected from the group consisting of a GSK3 inhibitor, a TGF-β inhibitor, a BMP inhibitor, a p53 inhibitor, a Notch inhibitor and a RAR agonist, or all members thereof. More preferably, the composition of the present invention comprises a GSK3 inhibitor, a TGF-β inhibitor, a p53 inhibitor, a Notch inhibitor, a RAR agonist, a PI3K inhibitor, and a cAMP inducer. In the composition of the present invention, it is particularly preferable to comprise a cAMP inducer or the inducer and a PI3K inhibitor.

Further, the present invention can also include a composition for producing an insulin-producing cell by inducing differentiation directly from a somatic cell, characterized by comprising a GSK3 inhibitor, a TGF-β inhibitor, a PI3K inhibitor, a Notch inhibitor, and a cAMP inducer. Hereinafter, such a composition is also referred to as the composition of the present invention.

The composition of the present invention may comprise at least any combination of the above, and may optionally further comprise other inhibitors, inducing agents, and the like, if necessary.

Each of the above inhibitors, inducers, and the like may be alone or a combination of two or more kinds.

Specific inhibitors and the like may have two or more kinds of inhibitory effects, and in this case, one inhibitor and the like may be considered to include a plurality of inhibitors and the like.

The above-mentioned specific examples and preferable examples of the inhibitors, the inducers, and the like are the same as those described above.

The composition of the present invention can be used as a composition for producing an insulin-producing cell from a somatic cell. The composition of the present invention can also be used as a medium for producing an insulin-producing cell from a somatic cell.

Examples of the medium used for the production of an insulin-producing cell from a somatic cell include a basal medium produced by mixing components required for cell culture, and a medium containing a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof as active ingredients. The above-mentioned active ingredient may be contained in a concentration effective for the production of an insulin-producing cell, and the concentration can be appropriately determined by a skilled person in the art. Basal media can be selected from known media or commercially available media. For example, MEM (Minimum Essential Medium), DMEM (Dulbecco's Modified Eagle Medium), DMEM/F12, RPMI1640, or a medium modified with these, which are conventional mediums, can be used as the base medium.

The medium may further be supplemented with known medium components as described hereinabove, such as serum, proteins such as albumin, transferrin, growth factors, etc., amino acids, sugars, vitamins, fatty acids, antibiotics, etc.

The medium may further be supplemented with a substance effective to induce differentiation into insulin-producing cells, as described hereinabove.

Furthermore, in the present invention, a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof can be administered to a living body to produce an insulin-producing cell from a somatic cell in the living body. That is, the present invention provides a process for producing an insulin-producing cell from a somatic cell in vivo, comprising administering a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof to a living organism. Preferred combinations of inhibitors and the like for administration to an organism are as described herein. Examples of the living body include humans, mammals other than humans, and animals other than mammals (birds, reptiles, amphibians, fish, etc.), but humans are particularly preferable. By administering a cAMP inducer, and six members selected from the group consisting of a GSK3 inhibitor, a TGF-β inhibitor, a BMP inhibitor, a p53 inhibitor, a PI3K inhibitor, a Notch inhibitor and a RAR agonist, or all members thereof to a specific site in a living body, an insulin-producing cell can be produced from a somatic cell at the specific site.

EXAMPLE

Hereinafter, the present invention will be illustrated in detail by examples and test examples, but the present invention is not limited to the ranges described in the examples and the like.

Example

Production of Insulin-Producing Cells

<Direct Induction from Human Fibroblasts to Insulin-Producing Cells>

(1) Human Fibroblasts

The human fibroblasts used as the material were purchased from DS Pharma Biomedical Co., Ltd. The fibroblasts are derived from 38-year-old human skin.

(2) Direct Induction from Human Fibroblasts into Insulin-Producing Cells.

The human fibroblasts were seeded in $5 \times 10^4$ portions in 35-mm dishes coated with gelatin (Cat #: 190-15805, manufactured by Wako Pure Chemical Co.) and cultured in DMEM medium (manufactured by Gibco) supplemented with 10% fetal bovine serum (Fetal bovine serum; FBS), 100 U/mL penicillin, and 100 μg/mL streptomycin at 37° C. under 5% $CO_2$ conditions until confluent. DMEM denotes Dulbecco's Modified Eagle Medium (Dulbecco's Modified Eagle Medium).

The medium for dishes of the human fibroblasts described above was replaced with a medium of DMEM/F12 (manufactured by Gibco) having 10% fetal bovine serum (FBS, manufactured by Hyclone), ITS-X (Cat #: 51500056, manufactured by Gibco), non-essential amino acids (NEAA: Non-essential amino acids; Cat #: 11140050, manufactured by Gibco), Glutamine (manufactured by Gibco; final concentration 2 mmol/L), nicotinamide (Cat #: 72340-100G, manufactured by Sigma-Aldrich; final concentration 10 mmol/L), Exendin-4 (Cat #: av120214, manufactured by Abcam; final concentration 100 ng/mL), 100 U/mL penicillin, 100 μg/mL streptomycin, and low molecular weight compounds described below. After that, the culture medium was changed every three days to the culture medium having the same composition, and the culture medium was cultured at 37° C. under 5% $CO_2$ conditions.

<Low Molecular Weight Compounds>

1 μM CHIR99021 (Cat #: 13122, Cayman Chemical)
2 μM SB431542 (Cat #: 198-16543, Wako)
1 μM LDN193189 (Cat #: 124-06011, Wako)
5 μM pifithrin-α (Cat #: 162-23133, Wako)
7.5 μM forskolin (Cat #: 063-02193, Wako)
2.5 μM LY294002 (Cat #: 70920, Cayman Chemical)
5 μM DAPT (Cat #: sc-201315, Santa Cruz Biotechnology)
1 μM retinoic acid (Cat #: 186-01114, Wako)

(3) Results

The results of culturing according to the above (2) are shown in Table 1. In the table, "+" indicates the presence of the compound in the medium, and "−" indicates the absence of the compound in the medium.

TABLE 1

| Chemical compound | function | Ex. 1 | Ex. 2 | Ex. 3 | Ex. 4 | Ex. 5 | Ex. 6 | Ex. 7 | Comp. Ex. 1 |
|---|---|---|---|---|---|---|---|---|---|
| CHIR99021 | GSK3 inhibitor | + | − | + | + | + | + | + | + |
| SB431542 | TGF-β inducer | + | + | − | + | + | + | + | + |
| LDN193189 | BMP inhibitor | + | + | + | − | + | + | + | + |
| Pifithrin-α | P53 inhibitor | + | + | + | + | − | + | + | + |
| Forskolin | cAMP inducer | + | + | + | + | + | + | + | − |
| LY294002 | PI3K inhibitor | + | + | + | + | + | − | + | + |
| DAPT | Notch inhibitor | + | + | + | + | + | + | − | + |

TABLE 1-continued

| Chemical compound | function | Ex. 1 | Ex. 2 | Ex. 3 | Ex. 4 | Ex. 5 | Ex. 6 | Ex. 7 | Comp. Ex. 1 |
|---|---|---|---|---|---|---|---|---|---|
| Retinoic acid | RAR agonist | + | + | + | + | + | + | + | + |
| Induction efficiency | Immuno staining, morphology | ○ | ○ | ○ | ◎ | ○ | △ | ○ | Dead |

Figure 2:
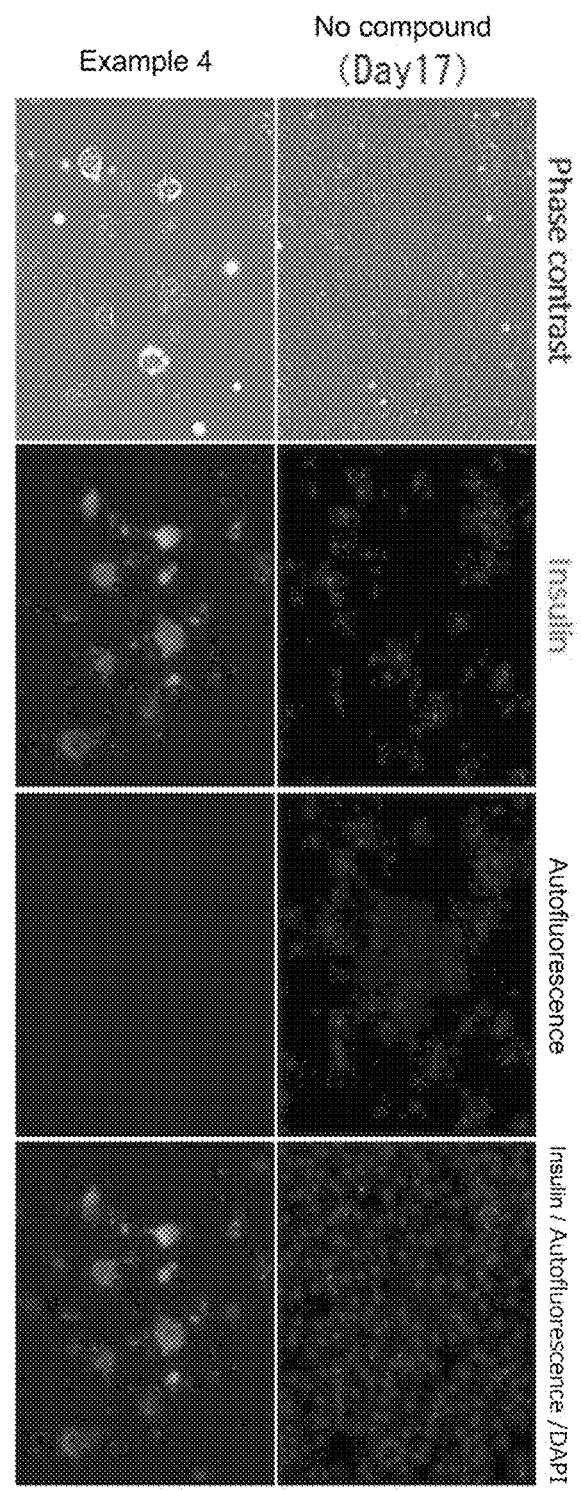
FIG. 2 is culture photographs (Phase contrast) of cells on the $17^{th}$ day after culturing by adding the compound, and the immune staining photographs. The four photographs on the left represent the results when the combination compound of Example 4 was added, and the four photographs on the right represent the results when the compound was not added.

Then, the cells were fixed with 4% paraformaldehyde on the 17$^{th}$ day after culturing with adding low molecular weight compounds, and immunostaining was carried out. For staining, anti-insulin antibodies (sc-9168, manufactured by Santa Cruz Biotechnology; used at 200-fold dilutions) were used. The results are shown in FIG. 2. In the drawing, green indicates results of insulin staining, and blue indicates nuclear staining with DAPI (4',6-diamidino-2-phenylindole). When FIG. 2 is displayed in gray, blue, green, and the like are not illustrated, but in the actual original color photograph, blue, green, and the like are illustrated.

Also, as shown in Table 1, the importance of the compounds required for conversion into cells expressing insulin was assessed at the 19$^{th}$ day after the start of culturing, by removing a compound one by one from the compounds of Example 1. The results are shown in FIGS. 3 and 4. Then, the amount of insulin secreted in the supernatant after 24 hours and the amount of insulin remaining in the cells after the measurement were quantified using Mercodia Ultrasensitive Insulin ELISA Kit (manufactured by Mercodia), and the amount was calculated as the amount per total protein 1 mg of the cells. The result is shown in FIG. 5. In the drawing, "8C-LDN, RA" indicates a combination eliminating LDN193189 and retinoic acid from the combination of compounds of Example 1.

(4) Evaluation of Insulin-Producing Cells

As shown in FIG. 1, after culturing with the addition of the low-molecular weight compound group, cells of a more spherical and smaller size appeared, which were clearly different in morphology from fibroblasts. As shown in FIG. 2, insulin staining was seen in certain numbers of these cells, and stronger staining was observed in the cytoplasm rather than in the nuclei of cells stained with DAPI. No clear autofluorescence overlapping with the insulin staining in green was observed in these cells. As is evident from Table 1 and FIGS. 3 and 4, forskolin (cAMP inducer) or LY294002 (PI3K inhibitor) was found to be of particular importance for conversion into cells expressing insulin.

As shown in FIG. 5, both the amount of insulin secreted in the supernatant and the amount of insulin remaining in intracellular after the measurement increased in the cells to which the compound was added.

Test Example

The cell culture was carried out by adding the following low-molecular-weight compound combinations in the same manner as in the above example. The human fibroblasts used as the material are fibroblasts derived from human skin of 0, 38 or 49 years of age purchased from DS Pharma Biomedical Co., Ltd. Then, the amount of insulin secreted in the supernatant after 24 hours with adding the compound group was quantified using Mercodia Ultrasensitive Insulin ELISA Kit (manufactured by Mercodia), and the amount was calculated as the amount per 10$^5$ cells (n=3). The result is shown in FIG. 6. The left figure shows the results with fibroblasts at age 0, the middle figure shows the results with fibroblasts at age 38, and the right figure shows the results with fibroblasts at age 49. In the figures, "no compound" indicates the result when the low molecular weight compounds are not added at all, and "5C" indicates the result when all of the low molecular weight compounds are added. Error bars represent standard deviations and asterisks represent significant differences (*P<0.05, **P<0.01) by Student's t-test.

<Low Molecular Weight Compounds>
3 μM CHIR99021 (Cat #: 13122, Cayman Chemical)
2 μM SB431542 (Cat #: 198-16543, Wako)
7.5 μM forskolin (Cat #: 063-02193, Wako)
5 μM LY294002 (Cat #:70920, Cayman Chemical)
5 μM DAPT (Cat #:sc-201315, Santa Cruz Biotechnology)

As shown in FIG. 6, the secreted amounts of insulin in the supernatants of all fibroblasts increased in the cells to which the low-molecular-weight compound group (5C) was added.

The invention claimed is:

1. A process for producing an insulin-producing cell by inducing differentiation directly from a fibroblast without performing artificial gene transfer, the process comprising culturing the fibroblast in the presence of:
   0.2 μmol/L to 50 μmol/L of at least one cAMP inducer;
   0.1 μmol/L to 20 μmol/L of at least one PI3K inhibitor; and
   five or all six members selected from the group consisting of
      0.1 μmol/L to 20 μmol/L of at least one GSK3 inhibitor,
      0.1 μmol/L to 30 μmol/L of at least one TGF-β inhibitor,
      0.1 μmol/L to 10 μmol/L of at least one BMP inhibitor,
      0.5 μmol/L to 30 μmol/L of at least one p53 inhibitor,
      0.2 μmol/L to 30 μmol/L of at least one Notch inhibitor and
      0.05 μmol/L to 10 μmol/L of at least one RAR agonist,
   wherein the GSK3 inhibitor comprises CHIR99021, the TGF-β inhibitor comprises SB431542, the p53 inhibitor comprises pifithrin, the PI3K inhibitor comprises LY294002, the Notch inhibitor comprises DAPT, the RAR agonist comprises retinoic acid or the cAMP inducer comprises forskolin.

2. The process for producing an insulin-producing cell according to claim 1, wherein the culturing comprises culturing the fibroblast in the presence of the GSK3 inhibitor, the TGF-β inhibitor, the p53 inhibitor, the Notch inhibitor, the RAR agonist, the PI3K inhibitor, and the cAMP inducer.

3. The process for producing an insulin-producing cell according to claim 1, wherein the fibroblast is cultured in the presence of the BMP inhibitor, and the BMP inhibitor comprises LDN193189.

4. The process for producing an insulin-producing cell according to claim 1, wherein the fibroblast is cultured in the presence of the GSK3 inhibitor, and the GSK3 inhibitor comprises CHIR99021.

5. A process for producing an insulin-producing cell by inducing differentiation directly from a fibroblast without performing artificial gene transfer, the process comprising culturing the fibroblast in the presence of 0.1 μmol/L to 20 μmol/L of at least one GSK3 inhibitor,
0.1 μmol/L to 30 μmol/L of at least one TGF-β inhibitor,
0.1 μmol/L to 20 μmol/L of at least one PI3K inhibitor,
0.2 μmol/L to 30 μmol/L of at least one Notch inhibitor, and
0.2 μmol/L to 50 μmol/L of at least one cAMP inducer,
wherein the GSK3 inhibitor comprises CHIR99021, the TGF-β inhibitor comprises SB431542, the PI3K inhibitor comprises LY294002, the Notch inhibitor comprises DAPT, or the cAMP inducer comprises forskolin.

6. A composition for producing an insulin-producing cell by inducing differentiation directly from a fibroblast without performing artificial gene transfer, the composition comprising:

0.2 μmol/L to 50 μmol/L of at least one cAMP inducer;
0.1 μmol/L to 20 μmol/L of at least one PI3K inhibitor; and
five or all six members selected from the group consisting of
0.1 μmol/L to 20 μmol/L of at least one GSK3 inhibitor,
0.1 μmol/L to 30 μmol/L of at least one TGF-β inhibitor,
0.1 μmol/L to 10 μmol/L of at least one BMP inhibitor,
0.5 μmol/L to 30 μmol/L of at least one p53 inhibitor,
0.2 μmol/L to 30 μmol/L of at least one Notch inhibitor and
0.05 μmol/L to 10 μmol/L of at least one RAR agonist,
wherein the GSK3 inhibitor comprises CHIR99021, the TGF-β inhibitor comprises SB431542, the p53 inhibitor comprises pifithrin, the PI3K inhibitor comprises LY294002, the Notch inhibitor comprises DAPT, the RAR agonist comprises retinoic acid, or the cAMP inducer comprises forskolin.

7. The composition according to claim 6, comprising the GSK3 inhibitor, the TGF-β inhibitor, the p53 inhibitor, the Notch inhibitor, the RAR agonist, the PI3K inhibitor, and the cAMP inducer.

8. The composition according to claim 6, wherein the composition comprises the BMP inhibitor, and the BMP inhibitor comprises LDN193189.

9. The process for producing an insulin-producing cell according to claim 1, wherein the fibroblast is cultured in the presence of the TGF-β inhibitor, and the TGF-β inhibitor comprises SB431542.

10. The process for producing an insulin-producing cell according to claim 1, wherein the fibroblast is cultured in the presence of the p53 inhibitor, and the p53 inhibitor comprises pifithrin.

11. The process for producing an insulin-producing cell according to claim 1, wherein the fibroblast is cultured in the presence of the Notch inhibitor, and the Notch inhibitor comprises DAPT.

12. A process for producing an insulin-producing cell by inducing differentiation directly from a fibroblast without performing artificial gene transfer, the process comprising culturing the fibroblast in the presence of:

an effective amount of one or more cAMP inducers;
an effective amount of one or more PI3K inhibitors;
an effective amount of one or more GSK3 inhibitors;
an effective amount of one or more TGF-β inhibitors; and
an effective amount of one or more Notch inhibitors,
wherein the GSK3 inhibitor comprises CHIR99021, the TGF-β inhibitor comprises SB431542, the PI3K inhibitor comprises LY294002, the Notch inhibitor comprises DAPT, or the cAMP inducer comprises forskolin.

13. The process according to claim 12, wherein the culturing further comprises culturing the fibroblast in the presence of an effective amount of one or more p53 inhibitors.

* * * * *